United States Patent
Harrison et al.

(10) Patent No.: US 8,359,105 B2
(45) Date of Patent: Jan. 22, 2013

(54) ELECTRICALLY CONDUCTIVE PATHWAYS IN MEDICAL DEVICES

(75) Inventors: Kent D. Harrison, Maple Grove, MN (US); Derek C. Sutermeister, Eden Prairie, MN (US); Tim Ostroot, Cokato, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 482 days.

(21) Appl. No.: 12/199,563

(22) Filed: Aug. 27, 2008

(65) Prior Publication Data

US 2010/0057174 A1 Mar. 4, 2010

(51) Int. Cl.
*A61N 1/00* (2006.01)
*A61M 5/00* (2006.01)

(52) U.S. Cl. .................. 607/116; 607/115; 604/264

(58) Field of Classification Search .......... 607/115–116; 604/264
See application file for complete search history.

(56) References Cited

U.S. PATENT DOCUMENTS

| 5,725,817 A | 3/1998 | Milder |
| 6,287,484 B1 * | 9/2001 | Hausslein et al. ............ 252/512 |
| 2008/0015517 A1 * | 1/2008 | Geistert et al. ................ 604/264 |

FOREIGN PATENT DOCUMENTS

| EP | 0101595 | 2/1984 |
| WO | 02/32497 | 4/2002 |
| WO | 02/055145 | 7/2002 |

OTHER PUBLICATIONS

An International Search Report for related PCT Application No. PCT/US2009/004842 dated Apr. 27, 2010. 21 pgs.

* cited by examiner

*Primary Examiner* — Niketa Patel
*Assistant Examiner* — Nicole F Lavert
(74) *Attorney, Agent, or Firm* — Brooks, Cameron & Huebsch, PLLC

(57) ABSTRACT

Apparatuses, systems, and methods for electrically conductive pathways in medical devices. One embodiment of a medical device can include an elongate polymeric body having a proximal end and a distal end. Discrete particles of an electrically conductive material in the elongate polymeric body can form an electrically conductive pathway that extends at least partially between the proximal end and the distal end of the elongate polymeric body.

9 Claims, 8 Drawing Sheets

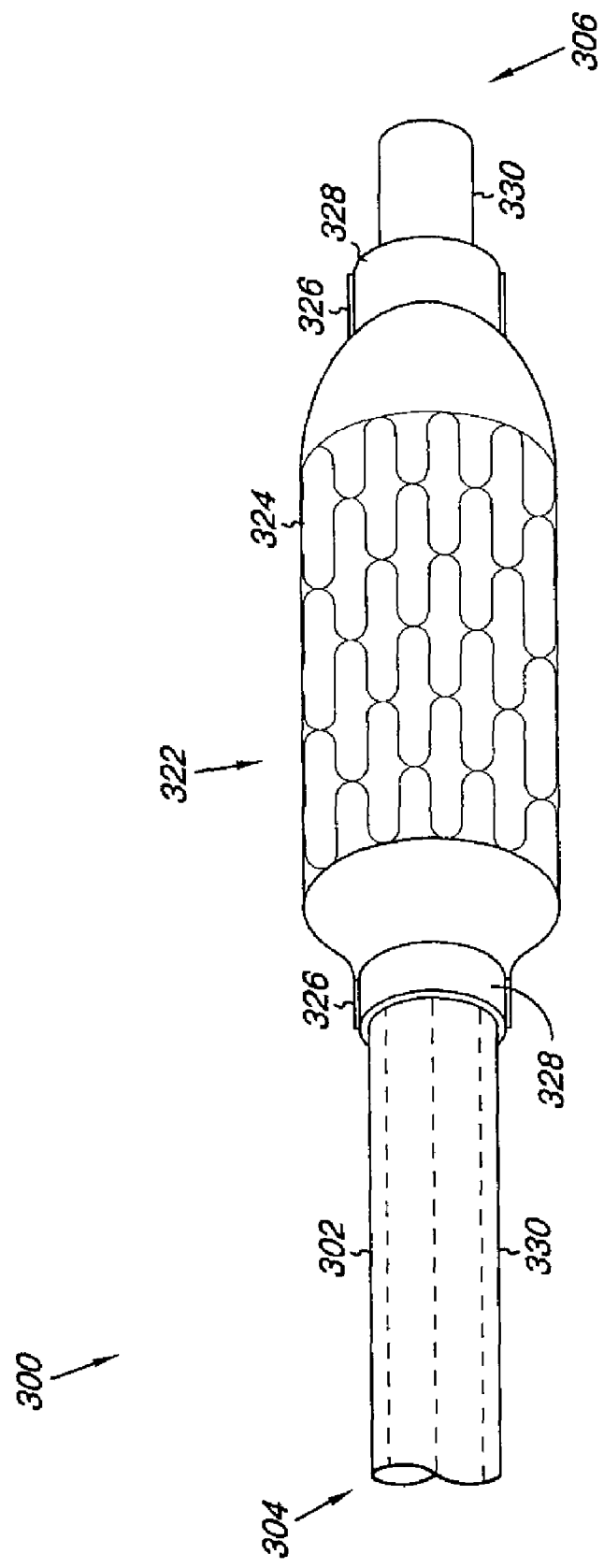

ELECTRICALLY CONDUCTIVE PATHWAYS IN MEDICAL DEVICES

TECHNICAL FIELD

The present disclosure relates generally to medical devices, and more particularly to implantable and/or insertable devices having electrically conductive pathways.

BACKGROUND

Intravascular diseases are commonly treated by relatively non-invasive techniques such as percutaneous transluminal angioplasty (PTA) and percutaneous transluminal coronary angioplasty (PTCA). These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to deliver an endoprosthesis such as a stent, graft, stent-graft, vena cava filter or other implantable device or devices, collectively referred to herein as a stent or stents. Where a stent is to be delivered into a body lumen the catheter may include one or more inflatable portions or balloons. Typically, the stent is retained in the pre-delivery state about the catheter shaft, or a portion thereof such as a balloon, by crimping and/or through the use of a retaining mechanism such as sleeve, sheath or sock.

Some of the above mentioned medical devices include electrically operable components. For example, U.S. patent application Pub. No. 2005/0165439 A1 teaches medical devices such as catheters, guidewires, and aneurysm coils, in which electrically actuated materials, such as electroactive polymers and piezoelectric materials, are used to enhance or expand functionality. U.S. patent application Pub. No. 2005/0187603 A1 teaches the use of electroactive polymer (EAP) materials in the form of a collar or balloon waist to provide a balloon with the ability to be selectively rotated about a catheter shaft. U.S. patent application Pub. No. 2008/0027377 A1 teaches a catheter shaft with an EAP wall that can provide a changeable diameter for a lumen. U.S. patent application Pub. No. 2008/0086081 A1 teaches an expandable medical balloon including an EAP material to provide for an expanded and deflated state of the balloon. U.S. Pat. No. 7,338,509 teaches the use of an EAP material in a device delivery sheath that volumetrically expands and contracts upon application of an appropriate electrical potential.

Medical devices that include electrically operable components include electrically conductive pathways to transmit and receive electrical signals to and from the component. For example, U.S. Pat. No. 5,476,502 teaches defibrillator and demand pacer catheters including an electrically conductive pathway comprised of a plurality of lead wires. U.S. patent application Pub. No. 2003/0139794 A1 teaches a body implantable lead including coil or multistrand cable conductors enclosed in a housing for transmitting electrical signals. U.S. patent application Pub. No. 2005/0187603 teaches one or more conductive wires that extend from a proximal region of a catheter to collars associated with the catheter and a balloon. The '7603 publication also teaches that the electric circuit including the conductive wires can be completed as a result of the presence of saline or other fluid of an electrically conductive nature which is used to expand the balloon.

BRIEF DESCRIPTION OF THE DRAWINGS

FIG. 3 illustrates an embodiment of the present disclosure in which the medical device is a balloon catheter.

DETAILED DESCRIPTION

Figure 1:
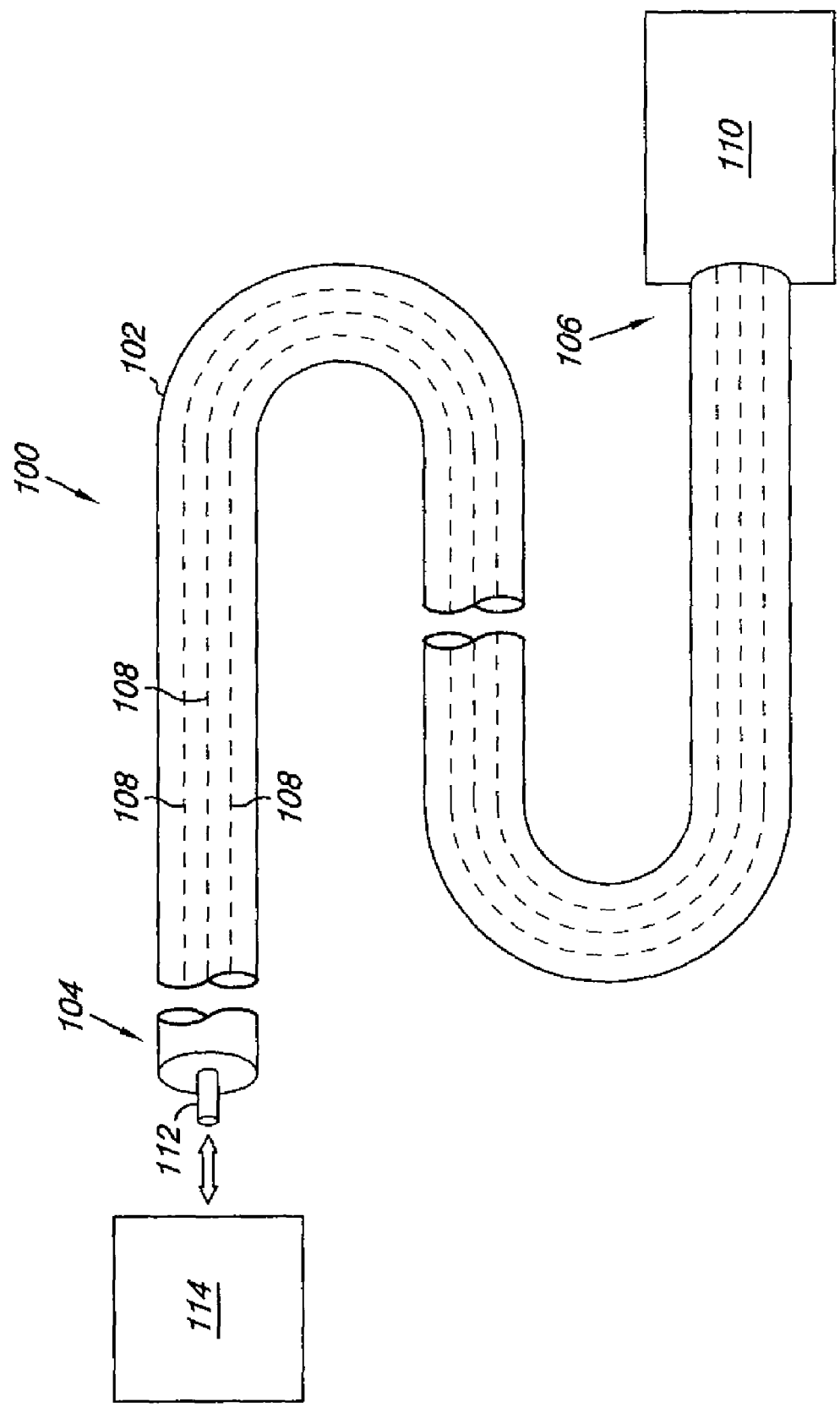
FIG. 1 illustrates embodiments of medical devices according to the present disclosure.

Embodiments of the present disclosure are directed to medical devices, systems, and methods for providing electrically conductive pathways in medical devices. For the various embodiments, discrete particles of an electrically conductive material can be used in an elongate polymeric body to provide an electrically conductive pathway that extends at least partially between a proximal end and a distal end of the elongate polymeric body. In additional embodiments, an electrically conductive liquid can be sealed in a container in an elongate polymeric body to provide an electrical pathway.

As used herein, the terms "a," "an," "one or more," and "at least one" are used interchangeably. Unless otherwise indicated, all numbers expressing quantities of ingredients, processing conditions, and so forth used in the disclosure and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, each numerical parameter should at least be construed in light of the number of reported significant digits and by applying ordinary rounding techniques.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of the present disclosure. In addition, as will be appreciated the proportion and the relative scale of the elements provided in the figures are intended to illustrate the embodiments of the present disclosure, and should not be taken in a limiting sense.

FIG. 1 illustrates an embodiment of a medical device 100 according to the present disclosure. As illustrated, the medical device 100 includes an elongate polymeric body 102 with a proximal end 104 and a distal end 106. The elongate polymeric body 102 further includes an electrically conductive pathway 108 that extends at least partially between the proximal end 104 and the distal end 106. In an additional embodiment, the electrically conductive pathway 108 extends from the proximal end 104 towards the distal end 106 of the elongate polymeric body 102, where it is possible for the electrically conductive pathway 108 to extend to the distal end 106. As discussed more fully herein, more than one electrically conductive pathway 108 can also be present in the elongate polymeric body 102, where each of the electrically conductive pathways 108 are electrically insulated from each other.

The medical device 100 further includes one or more electrically operable components 110. As illustrated, the electrically operable component 110 is associated at least partially with the elongate polymeric body 102. For the various embodiments, portions of the electrically operable component 110 that either require electrical energy to perform their intended function and/or that need to conduct electrical energy to perform their intended function are electrically coupled to the electrically conductive pathway 108. Such components can include electroactive polymers (EAPs), balloon assemblies, electrodes, and other electrically operable components as will be understood by one of ordinary skill in the art. Examples of such electrodes include pacing electrodes as are known, and electrodes associated with delivery of a therapeutic agent, for example, as taught in U.S. patent application Ser. No. 11/055,930, publication No. 2006/0184092, entitled "Internal Medical Devices for Delivery of Therapeutic Agent in Conjunction with a Source of Electrical Power," and filed Feb. 11, 2005. Embodiments are not limited to any specific examples described herein.

For the various embodiments, the medical device 100 can include an electrical connector 112. The electrical connector 112 is electrically coupled to the electrically conductive pathway 108. The electrical connector 112 allows the electrically operable component 110 to be electrically connected to a device 114. In an additional embodiment, the electrical connector 112 can be releasably connected to the device 114. For the various embodiments, the device 114 can provide and/or receive electrical energy from one or more portions of the electrically operable component 110 under predetermined conditions. For example, the device 114 can provide electrical energy from an associated power source such as a battery, a DC power connection, an AC power connection, or other power source. The device 114 can include software, application modules, application specific integrated circuit (ASIC) logic, and/or instructions storable in memory and executable by a processor to cause electrical energy to be provided to and/or for electrical energy received from the electrically operable component 110 to be analyzed and a return signal to be provided by the device 114. Examples of device 114 can include a pulse generator (e.g., a pacemaker), a power supply, a computing device, etc. One or more of the elongate polymeric body 102, the electrically operable component 110, and the device 114 can be implantable and/or insertable (e.g., percutaneously) in a patient.

As discussed herein, the electrically conductive pathway 108 can be formed using a variety of electrically conductive materials and manufacturing techniques. For example, the electrically conductive pathway 108 can include discrete particles of an electrically conductive material. In one embodiment, the discrete particles forming the electrically conductive pathway 108 can be embedded in the elongate polymeric body 102 at a density that is sufficient to allow for electrical energy to be conducted along the electrically conductive pathway 108. In one embodiment, the density of the discrete particles forming the electrically conductive pathway 108 can be sufficiently dense so that the discrete particles are in physical contact with adjacent discrete particles. In an additional embodiment, the discrete particles forming the electrically conductive pathway 108 can be present in a density that, while not necessarily providing for physical contact with an adjacent discrete particle, provides discrete particles that are sufficiently close to allow for electrical conductivity to be maintained along the electrically conductive pathway 108. One advantage of these configurations using the discrete particles is a potential to help reduce the likelihood of fracture of the conductor. That is, this structure can flex with reduced likelihood of fatigue fractures occurring.

For the various embodiments, the discrete particles forming the electrically conductive pathway 108 can be provided in the elongate polymeric body 102 during its formation. For example, the discrete particles can be co-extruded with the elongate polymeric body 102. In one embodiment, the discrete particles can be introduced (e.g., co-extruded) as a "vein" of material within a wall of the elongate polymeric body 102 to form the conductive pathway 108, such that the "vein" of discrete particles and the wall merge together into a substantially laminar structure.

In an additional embodiment, the discrete particles can be formed as a coating or a layer that at least partially surrounds an interior surface (e.g., a wall of a lumen) of the elongate polymeric body 102. In such embodiments the layer of discrete particles can be sandwiched between layers of the polymeric material of the elongate polymeric body 102, where the polymeric material can act as an electrical insulator for the conductive pathway 108. Such embodiments can be formed by coextruding the elongate polymeric body 102 in steps, where a central core of the elongate polymeric body 102 receives a coating of the discrete particles, which is then subsequently coated with another layer of the polymeric material so as to form the elongate polymeric body 102. In some embodiments, two or more "layers" of the discrete particles can be formed (e.g., as "veins," as "concentric rings," and/or as "eccentric rings") where the rings can be annular and/or semi-annular.

In an additional embodiment, the discrete particles of the electrically conductive pathway 108 can undergo post-extrusion processing in an effort to improve the electrical conductivity of the conductive pathway 108. For example, in one or more embodiments, a metal oxide (e.g., silver oxide) can be built into an extrusion and would be capable of clustering in the presence of ultraviolet light to provide one or more electrically conductive pathways 108 in the elongate polymeric body 102. In such embodiments, the elongate polymeric body 102 can be provided with a photoresist mask in a particular pattern such that an unmasked area represents the desired pattern of a number of electrically conductive pathways 108 to be formed. After ultraviolet irradiation, the unmasked portion can include metal oxide particles that have clustered sufficiently to provide a number of electrically conductive pathways 108.

The electrically conductive pathway 108 need not be formed linearly with respect to a longitudinal axis of the elongate polymeric body 102. The conductive pathway 108 can have a configuration that allows the elongate polymeric body 102 to be flexible. For example, the pathway 108 can be formed in helical or zigzag path to allow for greater flexibility (e.g., radial compressibility) or stretch to occur along the longitudinal axis of the body 102.

A variety of materials can be used for the discrete particles. Examples of such include particles of metal, metal alloys, oxides of metal and/or metal alloys, electrically conductive polymers etc. Examples include oxides of elements in Groups 2-14 (e.g., Be, Mg, Ca, Al, Sn, Cu, Ag, Au, An, Ti, Mo, Fe, or Ni, among others) such as, for example, aluminum oxide. Oxides including more than one metal (e.g., mixed oxides) can also be used, such as indium-tin-oxide and aluminum-tin-oxide. Another example of an electrically conductive material for use with one or more embodiments of the present disclosure includes nickel coated graphite. The conductive particles can be provided with a number of shapes and sizes. For example, the conductive particles can have an average particle size smaller than 200 microns, where conductive particles having an average particle size of 10 to 100 microns are suitable. Other average particle sizes are also possible.

In one or more embodiments, a first layer of discrete particles interspersed along the elongate polymeric body 102 can at least partially encircle a portion of the elongate polymeric body 102. In some embodiments, a second layer of the discrete particles interspersed along the elongate polymeric body 102 can at least partially encircle a second portion of the elongate polymeric body 102. Embodiments including more than one layer of discrete particles can have two or more layers of discrete particles electrically insulated from each other by the elongate polymeric body 102 or a separate insulating layer. Such a separate insulating layer can be co-extruded with, or bonded to, the elongate polymeric body 102.

One or more embodiments can include a layer of an electrically conductive polymer as the electrically conductive pathway 108, as discussed herein, formed over a portion of the polymeric body 102. For example, the layer of the electrically conductive polymer could be formed in and/or on the polymeric body 102 through a co-extrusion process, as discussed herein. In an additional embodiment, the electrically conductive polymer could be coated on an intermediate form of the polymeric body 102 (e.g., a central core of the polymeric body 102) by spray coating, sputter deposition, chemical vapor deposition, atomic layer deposition, among other techniques. The remainder of the polymeric body 102 could then be formed around the electrically conductive polymer in forming the polymeric body 102.

Suitable examples of electrically conductive polymers feature a conjugated backbone (e.g., they have a backbone that contains an alternating series of single and double carbon-carbon bonds). Examples of such electrically conductive polymers include, but are not limited to, polypyrroles and derivative thereof, polyanilines, polythiophenes, polyethylenedioxythiophenes, poly(p-phenylene vinylene)s, polysulfones, fluorophenyl thiophene, polyacetylenes, polyphenylene sulfide, polynaphthalene, and combinations thereof. In an additional embodiment, the electrically conductive polymers can be used in their pure form and/or used in a form that has undergone oxidation or reduction.

In an additional embodiment, one or more hypotubes can serve as the electrically conductive pathway 108, for the elongate polymeric body 102. Embodiments including multiple hypotubes can further include insulating layers to separate the multiple hypotubes. Such insulating layers can include co-extruded portions of the elongate polymeric body 102, as well as layers of other insulating material (e.g., a silicone rubber, a polyurethane, a polyimide, paraline or another biocompatible, electrically insulating material).

In general, a hypotube can impart an appropriate amount of stiffness to the elongate polymeric body 102 to help facilitate positioning (e.g., in a blood vessel) within a patient. Furthermore, a hypotube can include at least one slit extending at least partially through the tubular wall for increased flexibility (e.g., to help promote guidability of portions of the polymeric body 102 through a patient's vasculature). For example, the at least one slit can be characterized as a spiral cut extending along at least a portion of the hypotube. A hypotube can be made of a metal or an alloy, although in some cases hypotubes can be made of a polymer (e.g., one or more of the polymers discussed herein). Examples of alloy hypotube materials include nitinol and stainless steel (e.g., 303, 304, 316L). A hypotube may optionally be provided with a low friction coating such as polytetrafluoroethylene.

Combinations of the above embodiments provided herein could also be used in forming the conductive pathway 108 of the present disclosure. For example, it is possible that a combination of the discrete particles and the electrically conductive polymer could be used to form the conductive pathway 108 of the present disclosure. Other combinations of electrically conductive materials discussed herein are also possible.

The elongate polymeric body 102 according to the present disclosure, can be formed from a number of different polymeric materials. Examples include, but are not limited to, both non-elastomeric and elastomeric materials including, but not limited to, polyesters such as polyethylene terephthalate phthalate polyesters and copolyesters; poly-n-propylene terephthalate, polybutylene terephthalate, polyethylene naphthalate; polybutylene naphthalate; polyethers such as polyether-block-amides, polyether-polyesters and polyether-polyamide-polyester block copolymers, poly(butylene terephthalate)-block-poly(tetramethylene oxide) polymers, polyamides, nylons, polyurethanes including polyether urethanes block copolymers, polyester urethanes and polyureas, polyolefins such as polypropylene, polyethylene and so forth; polyolefin copolymers such as ethylene vinyl acetate; polybutylene naphthalate-polyether block copolymers; polymers of vinyl monomers such as polyvinyl chlorides and vinylidene fluorides, fluoropolymers including PTFE, FEP, poly(meth)acrylates, polycarbonates, copolymers thereof, and mixtures thereof. One of ordinary skill in the art would understand that this list is intended for exemplary purposes only, and is not an exclusive list. There are numerous other polymers that may be employed herein.

Figure 2:
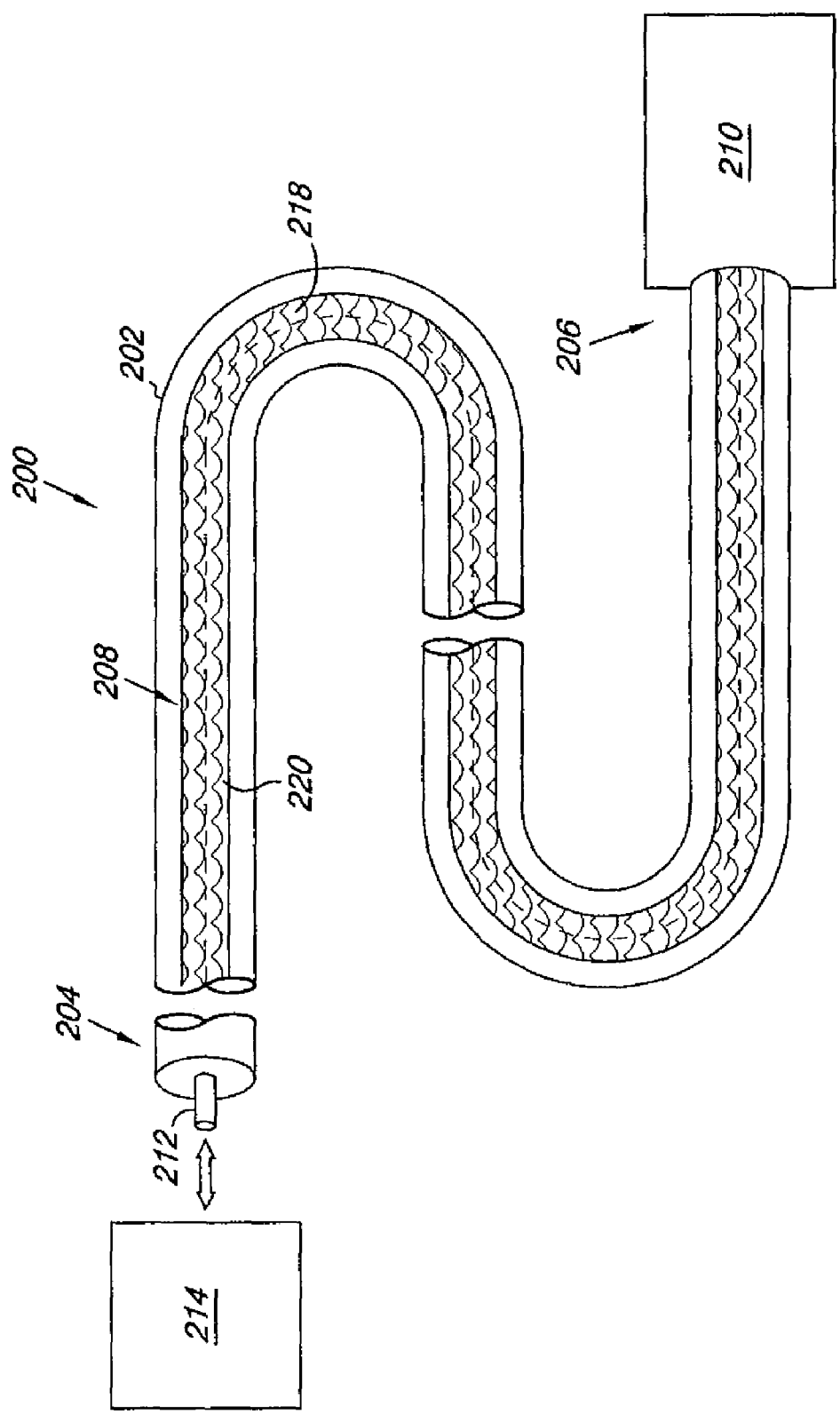
FIG. 2 illustrates embodiments of medical devices according to the present disclosure.

Referring now to FIG. 2, there is illustrated an additional embodiment of the medical device 200 according to the present disclosure. Medical device 200 includes the elongate polymeric body 202 with the proximal end 204 and the distal end 206. The elongate polymeric body 202 further includes the electrically conductive pathway 208 that extends at least partially between the proximal end 204 and the distal end 206. Also illustrated is the electrically operable component 210, as discussed herein.

The proximal end 204 of the elongate polymeric body 202 can further include an electrical connector 212 that can be used to electrically couple the electrically operable component 210 to the device 214, as discussed herein. A device 214 can be coupled to the elongate polymeric body 202 with an electrical connector 212 in a variety of ways. For example, in one embodiment the electrical connector 212 can be formed of an electrically conductive material (e.g., a metal, metal alloy and/or an electrically conductive polymer) that at least partially extends through the elongate polymeric body 202 to provide electrical conductivity with an electrically conductive liquid 218 in an elongate container 220.

For the various embodiments, the electrically conductive pathway 208 includes the electrically conductive liquid 218 sealed within the elongate container 220. In one embodiment, the elongate container 220 completely encloses and/or seals the electrically conductive liquid 218 within the elongate polymeric body 202. That is, the elongate container 220 remains sealed after inclusion of the electrically conductive liquid 218, particularly during operation of the medical device 200. In a number of embodiments, the elongate container 220 does not include a mechanism for removing the electrically conductive liquid 218 or inserting additional electrically conductive liquid 218 after the container 220 is sealed. Accordingly, after the electrically conductive liquid 218 is sealed in the container 220, no additional electrically conductive liquid 218 is added, nor is any liquid removed.

The volume of the electrically conductive liquid 218 can equal the volume of the container 220, both of which can remain constant. The electrically conductive liquid 218 can fill the container 220. Accordingly, the electrically conductive liquid 218 can be substantially static. That is, the mass flow rate of the electrically conductive liquid 218 can be substantially zero (i.e., the liquid 218 has a substantially zero velocity field associated with an arbitrary control volume that is larger than, for instance, a few molecules of the electrically conductive liquid 218) during normal operation of the medical device

200. In one or more embodiments the pressure of the electrically conductive liquid 218 is constant after it is sealed in the elongate container 220, and remains essentially constant along the entire length of the elongate container 220 during operation of the medical device 200 (e.g., during a balloon catheterization).

A variety of compositions for the electrically conductive liquids 218 are possible. For example, compositions for the electrically conductive liquid 218 can include electron conductors such as a metal, a metal alloy, or a combination thereof. Such metals, metal alloys, or combinations thereof can be in a neat form or in suspension where particles of the metals, metal alloys, or combinations thereof are dispersed in a liquid (such as an electrically conductive liquid discussed herein). Examples of useful metals and metal alloys include, but are not limited to, gallium, and various alloys formed from gallium, zirconium, indium, and tin, among others. In one embodiment, the electrically conductive liquid 218 can include ionic conductors. For example, the liquid 218 can include saline solution and electrolyte solutions, among other ionic liquids.

According to the present disclosure, using the electrically conductive liquid 218 sealed in the container 220 as the electrically conductive pathway 208 can provide a number of advantages. For example, the electrically conductive liquid 218 may be capable of carrying a higher conductive load. In addition, use of the electrically conductive liquid 218 can reduce the likelihood of fracture of the conductor.

Referring now to FIG. 3, there is illustrated an embodiment of the present disclosure in which the medical device 300 is a balloon catheter 322. As illustrated, the balloon catheter 322 includes an elongate polymeric body 302 having an electrically conductive pathway 308, as described herein. The elongate polymeric body includes a rotatable balloon 324 positioned around the polymeric body 302. The rotatable balloon 324 includes an inner surface that along with the elongate polymeric body 302 help to define an inflation chamber. The balloon catheter 322 further includes an inflation lumen that extends from the proximal end 304, towards the distal end 306, passing through the elongate polymeric body 302 to provide fluid communication to the inflation chamber. An inflation device, as are known, can be used to inflate the rotatable balloon 324.

The balloon, in its deflated state, can rotate around one or more shafts of the elongate body 302. The balloon can have waists 326 at either longitudinal end that are disposed about collars 328 on the elongate body 302. As illustrated in FIG. 3, waists 326 are shown from a cutaway perspective so as not to obscure the illustration of the collars 328. In one embodiment, the waists 326 can rotate about the collars 328, where the collars 328 are fixed to shaft 330 of the elongate body 302. In another embodiment, the waists 326 can be fixed to the collars 328 where the collars 328 can rotate about one or more shafts 330 of the elongate body 302. The collars 328 can "expand" to seat against the waists 326 of the balloon 324 to form a seal that allows for inflation fluid being delivered to balloon 324 to cause the balloon to inflate 324.

Systems employing such collars are featured in U.S. patent application Ser. No. 10/785,449, publication No. 2005/0187602, entitled "Rotatable Catheter Assembly," and filed Feb. 24, 2004. Another example of a rotatable balloon assembly is provided in U.S. patent application Ser. No. 12/199,720, entitled "Electroactive Polymer Activation System for a Medical Device", and filed concurrently with the present application.

As described in the aforementioned U.S. applications, collars 328 are at least partially constructed of an electro-active polymer (EAP) which expands to a predetermined extent upon exposure to electrical energy (e.g., an electrical current provided by an electrically conductive pathway 308). In some embodiments the EAP material of the collar 328 and/or the collar 328 itself can expand about 0.5% to about 20% expansion in a predetermined manner and/or direction when subjected to an electric current (e.g., a current of 0.001 micro-Amps to 1 milliAmps at −2 to +2 V). In one or more embodiments a collar 328 can be constructed of one or more conductive elements such as gold, silver, platinum, etc., which can be at least partially surrounded by a layer of EAP material.

In embodiments where the collars 328 are fixed to the catheter shaft 330, prior to exposure to the electric current the collars 328 can define an outside diameter that is sufficiently less than the inner diameter of the balloon waists 326 which are respectively disposed there about so as to allow the waists 326, and thus the balloon body extending there between, to freely rotate about the collars 328. When the collars 328 are exposed to the electric current through the electrically conductive pathway 308, the collars 328 can expand and thus effectively push against the respective balloon waists 326, effectively sealing the interior of the balloon which may then receive a fluid under pressure to inflate the balloon 324.

Referring now to FIGS. 4A-4E, there are illustrated cross sectional views of embodiments of an elongate polymeric body, such as the examples of elongate polymeric bodies illustrated in FIGS. 1-3, according to the present disclosure. As noted above, although particular electrically conductive pathways have been illustrated in association with particular elongate polymeric bodies, embodiments are not so limited. Unless otherwise noted, the electrically conductive pathways described herein (e.g., discrete particles of an electrically conductive material, an electrically conductive liquid sealed in a container, hypotubes, etc.) can be used with a number of elongate polymeric bodies that utilize electrical energy or that are connected to components that utilize electrical energy. Accordingly, the following descriptions of corresponding cross-sectional views of elongate polymeric bodies are not to be limited to a particular type of electrically conductive pathway or to a particular type of elongate polymeric body (e.g., a catheter, a lead, etc.).

As noted above, drawings illustrated herein are not necessarily to scale and certain components of a particular figure may be drawn out of proportion for ease of illustration and/or to provide clarity. Although specific examples of electrically activated devices may be described in association with FIGS. 4A-4E, embodiments are not so limited. It is intended that embodiments of electrically conductive pathways described herein can be used in association with various electrically operable components.

Figure 4A:
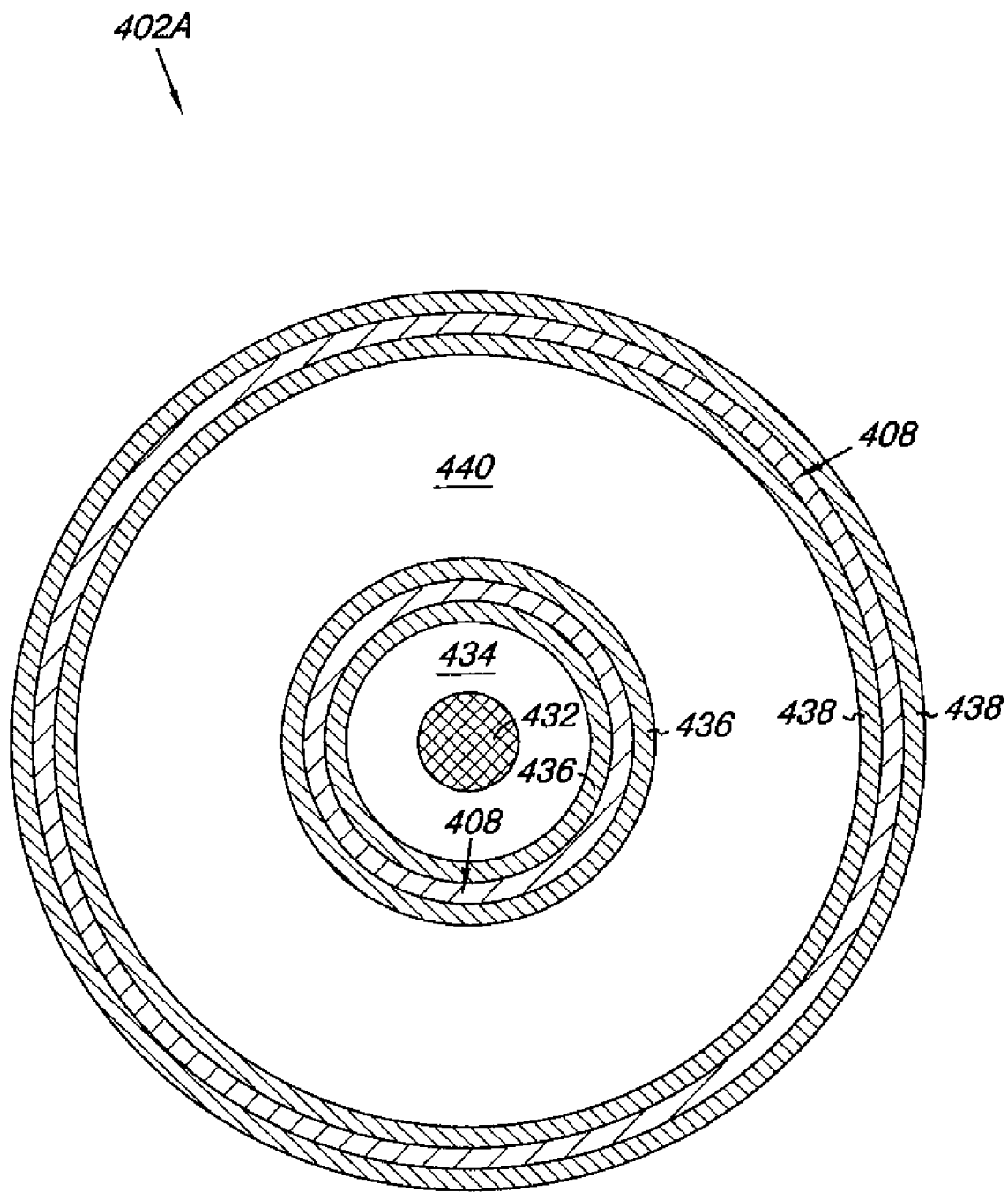
FIGS. 4A-4E illustrate cross sectional views of embodiments of an elongate polymeric body according to the present disclosure.

FIG. 4A illustrates a cross sectional view of an elongate polymeric body 402A according to the present disclosure. The embodiment illustrated in FIG. 4A can include a guide wire 432 and a guide wire lumen 434 defined by an inner wall 436. As will be appreciated by one of ordinary skill in the art, the configuration and location of the guide wire lumen 434 relative the elongate body 402A can be dependent upon the associated medical device. Examples of possible guide wire lumen 434 configurations include, but are not limited to, an over-the-wire design, a rapid-exchange, and/or a single-operator-exchange design.

The elongate polymeric body 402A can include an outer wall 438 which, in connection with inner wall 436, defines an inflation lumen 440. The inflation lumen 440 can extend from the proximal end of the elongate polymeric body 402A to be in fluid communication with an interior chamber of an inflatable balloon to allow the balloon to be inflated and deflated.

One or more of the inner wall 436 and outer wall 438 can include one or more layers of conductive particles, as discussed herein, that form one or more conductive pathways 408 in the elongate polymeric body 402A. In some embodiments, a layer of conductive particles can be co-extruded with the inner wall 436 and/or outer wall 438 during fabrication of the elongate polymeric body 402A, as discussed herein. That is, conductive particles can be interspersed within the inner wall 436 and/or outer wall 438 during extrusion. As such, the inner wall 436 and/or outer wall 438 within which the conductive particles are interspersed can act as an electrical insulator between the conductive pathways 408 and other components of the elongate polymeric body 402A. Electrical contacts can be formed with conductive pathways 408 to provide power to one or more electrically operable components associated with a device that includes elongate polymeric body 402A.

Figure 4B:
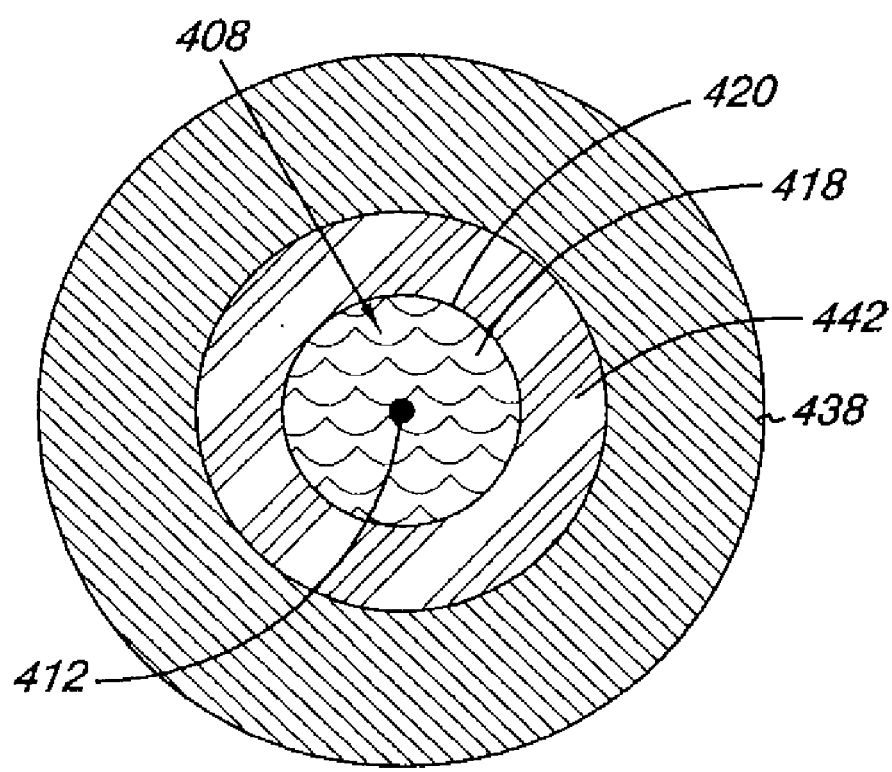

In an additional embodiment, FIG. 4B illustrates a cross sectional view of an elongate polymeric body 402B according to the present disclosure. The elongate polymeric body 402B includes an outer wall 438 and an insulating layer 442 that defines a container 420, as discussed herein. An electrically conductive liquid 418, as discussed herein, can be sealed in the container 420 to form an electrically conductive pathway 408 through the elongate polymeric body 402B. The insulating layer 442 can be co-extruded with the outer wall 438 during fabrication of the elongate polymeric body 402B. The insulating layer 442 can be formed of a non-conductive material (e.g., a dielectric, for example, a polymeric material). In one or more embodiments, the insulating layer 442 can be a silicone rubber, a polyurethane, or a polyimide. A solid electrical connector 412 can extend through at least a portion of the elongate polymeric body 402B to provide an electrical pathway to the electrically conductive liquid 418 in container 420.

The electrically conductive liquid 418 sealed in container 420 can be used to provide electrical energy to one or more electrically operable components associated with the elongate polymeric body 402B. For example, the elongate polymeric body 402B can include electrically conductive polymers at or near an exterior surface at one or more points between the proximal and distal ends of the elongate polymeric body 402B. Electrically operable components can receive electrical energy from the electrically conductive liquid 418 either by direct contact with the liquid, or via a separate conductive member that contacts both the liquid 418 and the electrically operable component.

Figure 4C:
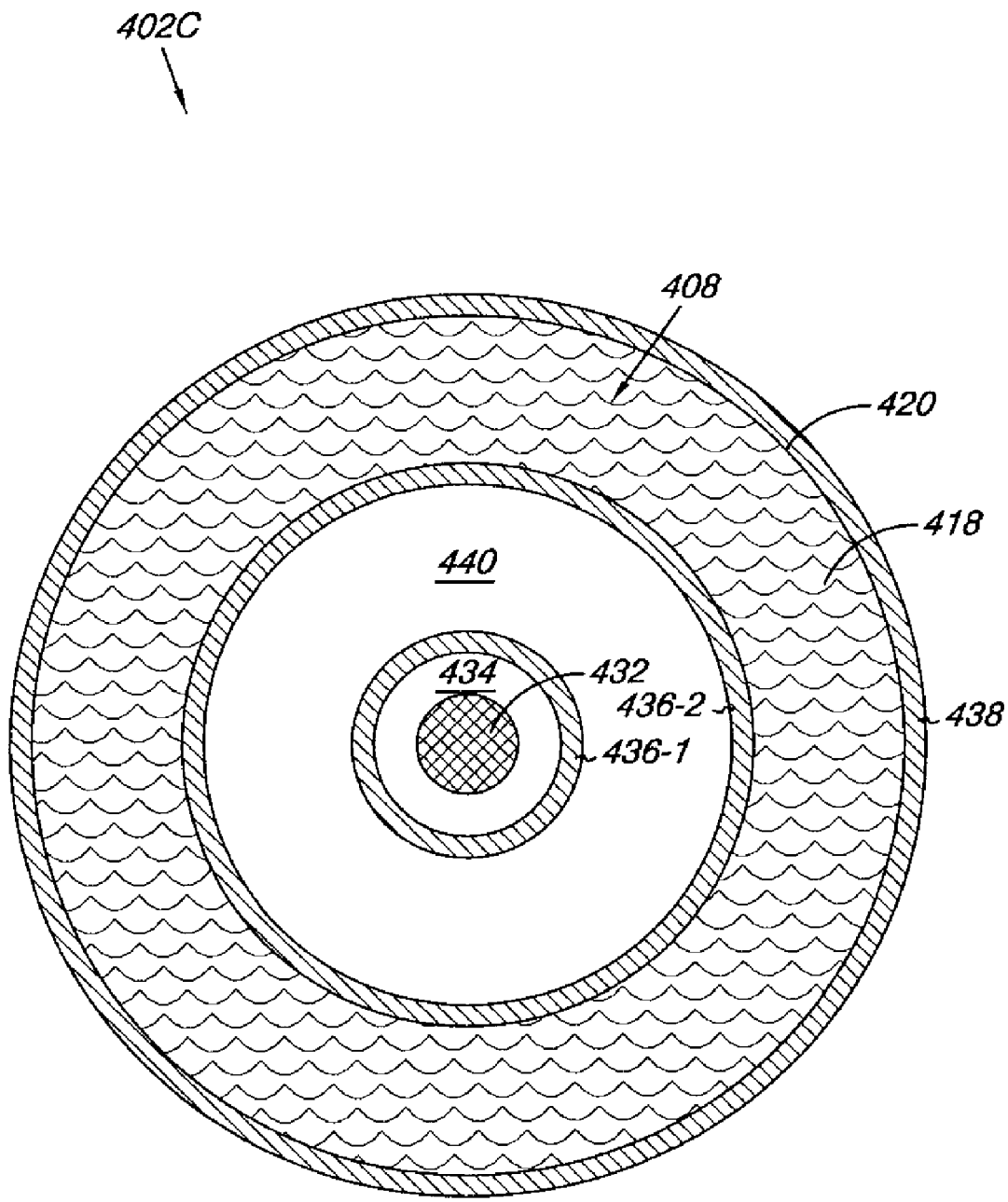

FIG. 4C illustrates a cross sectional view of an additional embodiment of an elongate polymeric body 402C according to the present disclosure. The embodiment illustrated in FIG. 4C can include a guide wire 432 and a guide wire lumen 434. The elongate polymeric body 402C can include a first inner wall 436-1 that defines the guide wire lumen 434. The elongate polymeric body 402C can include a second inner wall 436-2, which, in connection with the first inner wall 436-1, defines an inflation lumen 440. The elongate polymeric body 402C can further include a container 420 between the second inner wall 436-2 and the outer wall 438 that can include an electrically conductive liquid 418 sealed therein. As discussed herein, the electrically conductive liquid 418 can form an electrically conductive pathway 408 through the elongate polymeric body 402C.

Figure 4D:
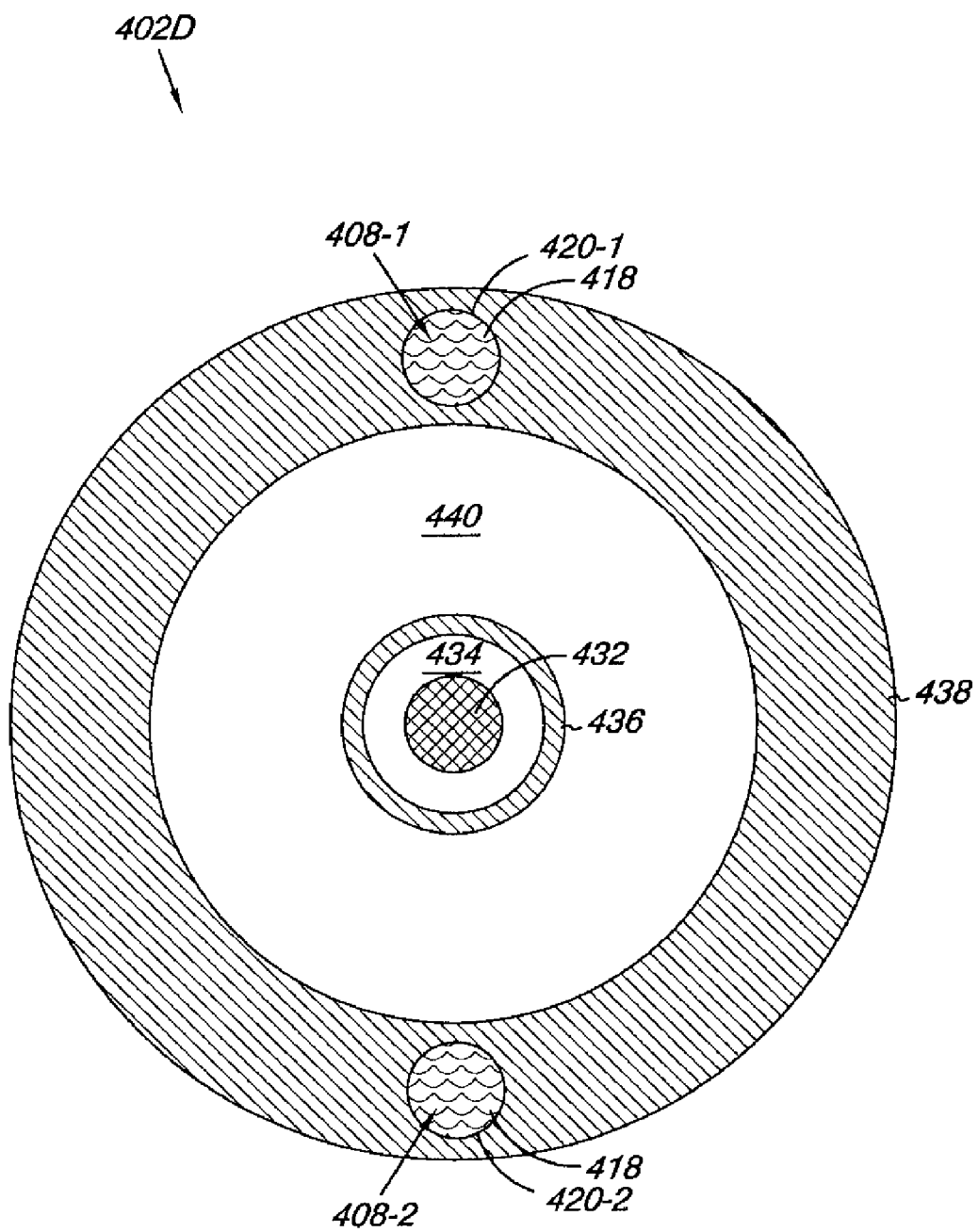

FIG. 4D illustrates a cross sectional view of an additional embodiment of an elongate polymeric body 402D according to the present disclosure. The embodiment illustrated in FIG. 4D can include a guide wire 432 and a guide wire lumen 434 defined by inner wall 436. The elongate polymeric body 402D can include an outer wall 438, which, together with inner wall 436, defines an inflation lumen 440. As noted above, the embodiment illustrated in FIG. 4D is not necessarily drawn to scale (e.g., in some embodiments, the radial thickness of inner wall 436 can be equal to the radial thickness of outer wall 438).

The elongate polymeric body can include a number of containers (e.g., containers 420-1 and 420-2) within outer wall 438 that can each include an electrically conductive liquid 418 sealed therein to form electrically conductive pathways (e.g., electrically conductive pathways 408-1 and 408-2) through the elongate polymeric body 402D.

Figure 4E:
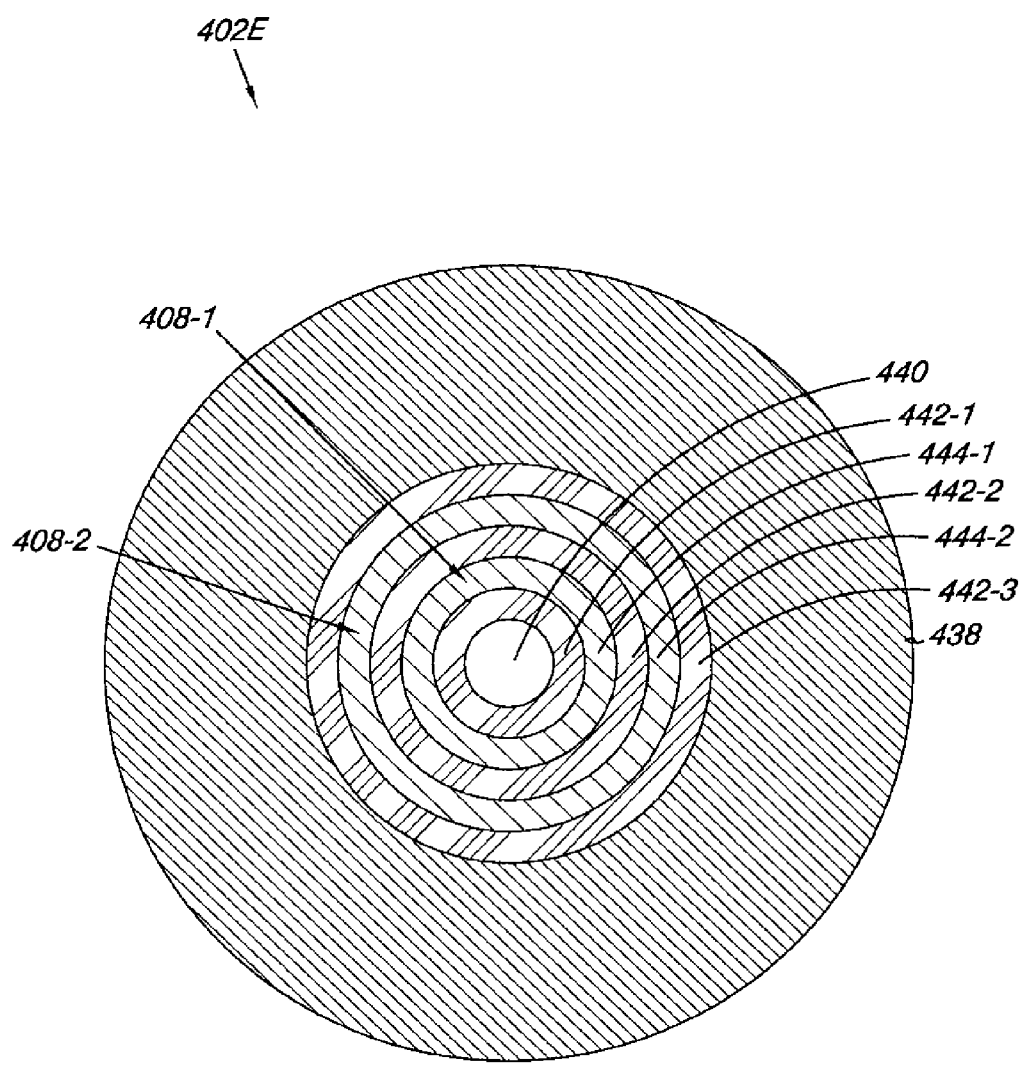

FIG. 4E illustrates a cross sectional view of an additional embodiment of an elongate polymeric body 402E according to the present disclosure. The elongate polymeric body 402E can include an outer wall 438 and a number of hypotubes (e.g., hypotube 444-1 and hypotube 444-2). Although two hypotubes 444-1 and 444-2 are illustrated, embodiments are not so limited. Elongate polymeric bodies, according to the present disclosure, can include greater or fewer than two hypotubes. The number of hypotubes can be separated by insulating layers (e.g., insulating layers 442-1, 442-2, and 442-3). The insulating layers can insulate the hypotubes from each other, as well as from the outer wall 438, and the inflation lumen 440. The insulating layers 442-1, 442-2, and 442-3 can be made of a number of materials as described herein. Each insulating layer need not be made of a same material as other insulating layers (e.g., insulating layer 442-1 may be formed of a different material than insulating layer 442-2).

Hypotubes 444-1 and 444-2 can be made of a number of materials as described herein. Hypotubes 444-1 and 444-2 can serve as electrically conductive pathways 408-1 and 408-2 for the elongate polymeric body 402E. For example, hypotube 444-1 can be electrically coupled to a device (not illustrated) to be in electrical communication with one or more electrically operable components associated with the elongate polymeric body 402E. In one or more embodiments, hypotubes can be reversibly or selectively coupled to a power source so as to allow an operator to control electrically operable components associated with the hypotubes.

While the present disclosure has been shown and described in detail above, it will be clear to the person skilled in the art that changes and modifications may be made without departing from the spirit and scope of the disclosure. As such, that which is set forth in the foregoing description and accompanying drawings is offered by way of illustration only and not as a limitation. The actual scope of the disclosure is intended to be defined by the following claims, along with the full range of equivalents to which such claims are entitled. In addition, one of ordinary skill in the art will appreciate upon reading and understanding this disclosure that other variations for the disclosure described herein can be included within the scope of the present disclosure.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A medical device, comprising:
    an elongate polymeric body having a proximal end and a distal end; and
    an electrically conductive pathway formed of discrete particles of one electrically conductive material in the elongate polymeric body that extends at least partially between the proximal end and the distal end of the elongate polymeric body;
    wherein adjacent discrete particles are not in physical contact.

2. The medical device of claim 1, where the one electrically conductive material is an electrically conductive polymer.

3. The medical device of claim 2, where the electrically conductive polymer is selected from the group consisting of polyaniline, polyacetylene, polypyrolle, polythiophene, fluorophenyl thiophene, polyphenylene vinylene, polyphenylene sulfide, polynaphthalene, polyphenylene, and combinations thereof.

4. The medical device of claim 1, where the one electrically conductive material is selected from the group consisting of a metal, a metal oxide, and a combination thereof.

5. The medical device of claim 1, where the elongate polymeric body includes a first layer of the discrete particles interspersed in the elongate polymeric body that at least partially encircles a portion of the elongate polymeric body.

6. The medical device of claim 5, including a second layer of the of the discrete particles interspersed in the elongate polymeric body that at least partially encircles a second portion of the elongate polymeric body, where the first layer and the second layer of the discrete particles interspersed in the elongate polymeric body are electrically insulated from each other by the elongate polymeric body.

7. The medical device of claim 1, wherein the one electrically conductive material comprises silver oxide clustered by ultraviolet irradiation to form the electrically conductive pathway.

8. The medical device of claim 1, wherein:
    the elongate polymeric body is provided with a photoresist mask in a particular pattern such that unmasked portions of the elongate polymeric body represent a pattern of the electrically conductive pathway; and
    the one electrically conductive material comprises silver oxide.

9. The medical device of claim 8, wherein:
    portions of the elongate polymeric body underlying the photoresist mask include unclustered silver oxide; and
    the electrically conductive pathway comprises clustered silver oxide.

* * * * *